US009722519B2

(12) United States Patent
Shreve et al.

(10) Patent No.: US 9,722,519 B2
(45) Date of Patent: *Aug. 1, 2017

(54) INTAKE PROFILE FOR OPTIMIZED UTILIZATION OF MOTOR CHARACTERISTICS

(71) Applicant: Waters Technologies Corporation, Milford, MA (US)

(72) Inventors: Joshua A. Shreve, Franklin, MA (US); Steven J. Ciavarini, Natick, MA (US)

(73) Assignee: WATERS TECHNOLOGIES CORPORATION, Milford, MA (US)

( * ) Notice: Subject to any disclaimer, the term of this patent is extended or adjusted under 35 U.S.C. 154(b) by 188 days.

This patent is subject to a terminal disclaimer.

(21) Appl. No.: 14/463,149

(22) Filed: Aug. 19, 2014

(65) Prior Publication Data

US 2015/0008862 A1 Jan. 8, 2015

Related U.S. Application Data

(63) Continuation of application No. 13/063,291, filed as application No. PCT/US2009/056438 on Sep. 10, 2009, now Pat. No. 8,829,844.

(Continued)

(51) Int. Cl.
*H02P 8/14* (2006.01)
*F04B 17/03* (2006.01)
(Continued)

(52) U.S. Cl.
CPC ............... *H02P 8/14* (2013.01); *F04B 17/03* (2013.01); *F04B 49/065* (2013.01);
(Continued)

(58) Field of Classification Search
CPC ...................................................... H02P 8/14
(Continued)

(56) References Cited

U.S. PATENT DOCUMENTS 4,568,866 A 2/1986 Floro et al.
4,714,867 A 12/1987 Palmin et al.
(Continued)

FOREIGN PATENT DOCUMENTS

EP 0085171 A2 8/1983

OTHER PUBLICATIONS

International search report on Patentability in related international patent application No. PCT/US09/56438, mailed on Nov. 5, 2009; 2 pages.

(Continued)

*Primary Examiner* — Kawing Chan
(74) *Attorney, Agent, or Firm* — Schmeiser, Olsen & Watts LLP

(57) ABSTRACT

Systems and methods for operating a stepper motor of a pump at a desired low velocity include memory for storing information corresponding to an intake velocity profile. The intake velocity profile represents an optimized acceleration curve for operating the stepper motor over a range of motor velocities during an intake cycle. A processor of a system controller dynamically accesses the memory during the intake cycle to acquire the information representing the intake velocity profile and issues a series of pulses to the stepper motor based on this information. In response to the pulses, the stepper motor accelerates in accordance with the optimized acceleration curve represented by the intake velocity profile. The optimized acceleration curve is based on the available torque of the stepper motor across a range of motor velocities and enables the motor to operate with greater torque utilization and less margin than traditional linear acceleration profiles.

19 Claims, 10 Drawing Sheets

Related U.S. Application Data

(60) Provisional application No. 61/096,455, filed on Sep. 12, 2008.

(51) Int. Cl.
*F04B 49/06* (2006.01)
*G01N 30/34* (2006.01)
*G01N 30/32* (2006.01)

(52) U.S. Cl.
CPC ............... *F04B 2203/0207* (2013.01); *F04B 2203/0209* (2013.01); *G01N 30/34* (2013.01); *G01N 2030/326* (2013.01)

(58) Field of Classification Search
USPC .......................................................... 318/696
See application file for complete search history.

(56) References Cited

U.S. PATENT DOCUMENTS

| | | |
|---|---|---|
| 4,797,207 A | 1/1989 | Honganen et al. |
| 4,990,058 A | 2/1991 | Eslinger |
| 5,522,555 A | 6/1996 | Poole |
| 5,676,225 A * | 10/1997 | Miyata ................ F16H 7/02 192/41 R |
| 5,889,379 A | 3/1999 | Yanagi et al. |
| 2008/0268978 A1 | 10/2008 | Hawkins et al. |

OTHER PUBLICATIONS

Notice of Allowance in related U.S. Appl. No. 13/063,291, mailed on Jun. 9, 2014; 13 pages.
Extended European Search Report in counterpart European Patent Application No. 09813571.8, mailed on Aug. 3, 2016; 8 pages.

* cited by examiner

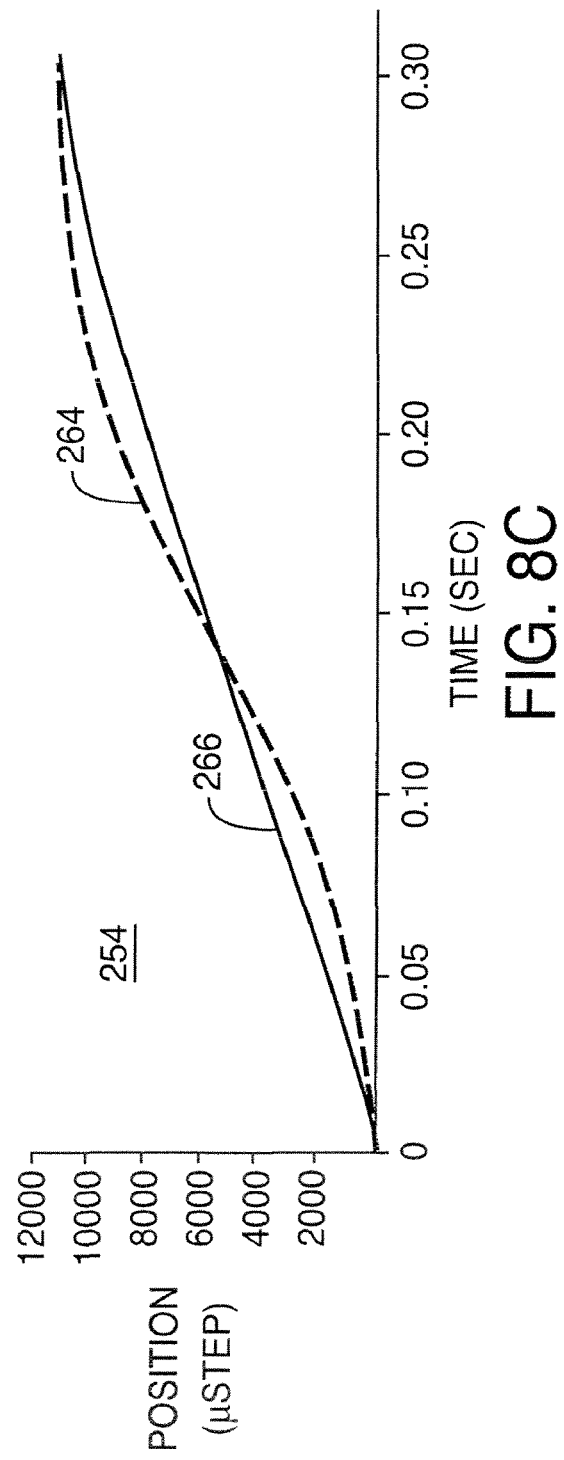

INTAKE PROFILE FOR OPTIMIZED UTILIZATION OF MOTOR CHARACTERISTICS

CROSS REFERENCE TO RELATED APPLICATIONS

This application is a continuation patent application of U.S. patent application Ser. No. 13/063,291 filed Mar. 10, 2011, which is the national stage of International Application No. PCT/US2009/056438, filed Sep. 10, 2009 and designating the United States, which claims priority to and the benefit of the filing date of U.S. Provisional Patent Application No. 61/096,455, filed on Sep. 12, 2008. The contents of these applications are expressly incorporated herein by reference in their entireties.

FIELD OF THE INVENTION

The invention relates generally to fluid delivery systems such as liquid chromatography systems. More specifically, the invention relates to systems and methods for optimizing utilization of a pump motor's acceleration capabilities during fluid intake cycles.

BACKGROUND

The mixing of liquids in controlled proportions is the keystone of many applications, a primary example of which is liquid chromatography. In a liquid chromatography application, a pump module intakes and delivers a mixture of liquid solvents and an injected sample to a point of use, such as a column of particulate matter. By passing the mixture through the column, the various components in the sample separate from each other at different rates and thus elute from the column at different times. A detector receives the elution from the column and produces an output from which the identity and quantity of the analytes may be determined. In an isocratic chromatography application, the composition of the liquid solvents remains unchanged, whereas in a gradient chromatography application, the solvent composition varies over time.

The reliability of the results produced by a chromatography application depends heavily on run-to-run reproducibility. In particular, the identification of sample analytes depend on the retention times of the detected elution peaks. Some pumping systems exhibit non-ideal pump characteristics, such as fluctuations in solvent composition and fluctuations in flow rate. These non-ideal pump characteristics can lead to undesirable separation performance and unreliable run-to-run reproducibility. In general, the greater the intake velocity of a pump module, the lower is the accuracy of solvent composition because of pump errors, such as bubble formation (outgassing) and timing errors related to valve switching. Accordingly, the benefits of a low intake velocity are a reduction in time-based errors and in pressure drop, thus in the out-gassing and cavitation of the intake fluidics.

SUMMARY

In one aspect, the invention features a method for operating a stepper motor of a pump during a fluid intake cycle. Available torque of the stepper motor is measured across a range of motor velocities within which the stepper motor will operate during the intake cycle. A maximum acceleration rate is calculated for each of a plurality of motor velocities in the range of motor velocities based on the available torque of the stepper motor measured at that motor velocity. An intake velocity profile is generated based on the maximum acceleration rates calculated for the plurality of motor velocities. The stepper motor is accelerated during the intake cycle in accordance with the generated intake velocity profile.

In another aspect, the invention features a method for operating a pump in a pumping system. The pump has a stepper motor coupled to a reciprocating plunger mechanism. The stepper motor moves the plunger mechanism within a chamber into which fluid is drawn during a draw stroke of the plunger mechanism. The method includes storing information, in memory, corresponding to an intake velocity profile that represents an optimized acceleration curve based on available torque for operating the stepper motor over a range of motor velocities at which the stepper motor will operate during an intake cycle. The memory is dynamically accessed during the intake cycle to acquire the information representing the intake velocity profile. A series of pulses is issued to the pump based on the information accessed in the memory. The stepper motor is accelerated, in response to the series of pulses, such that the stepper motor accelerates during the intake cycle in accordance with the optimized acceleration curve represented by the intake velocity profile.

In still another aspect, the invention features a pumping system comprising a pump having a stepper motor coupled to a reciprocating plunger mechanism. The stepper motor moves the plunger mechanism within a chamber into which fluid is drawn during a draw stroke of the plunger mechanism. Memory stores information corresponding to an intake velocity profile. The intake velocity profile represents an optimized acceleration curve based on available torque for operating the stepper motor over a range of motor velocities at which the stepper motor will operate during an intake cycle. A system controller has a processor that is in communication with the stepper motor to issue pulses thereto and with the memory to access dynamically during the intake cycle the information representing the intake velocity profile. The system controller determines from the accessed information when to issue pulses to the pump. The issued pulses cause the stepper motor to accelerate in accordance with the optimized acceleration curve represented by the intake velocity profile.

BRIEF DESCRIPTION OF THE DRAWINGS

The above and further advantages of this invention may be better understood by referring to the following description in conjunction with the accompanying drawings, in which like numerals indicate like structural elements and features in various figures. The drawings are not necessarily to scale, emphasis instead being placed upon illustrating the principles of the invention.

FIG. 8A, FIG. 8B, and FIG. 8C are a set of charts comparing an optimized intake velocity profile with a trapezoidal intake velocity profile with respect to acceleration, velocity, and stepper motor position.

DETAILED DESCRIPTION

Piston pumps operating in accordance with an intake velocity profile of the present invention optimize use of their stepper motors' acceleration capabilities during fluid intake cycles. Although described herein primarily with reference to low-pressure gradient pumps, the principles of the invention can be used for any piston pump intake velocity profile. For low-pressure gradient systems generally, flow and composition errors scale proportionately to the maximum velocity reached by the stepper motor during a fluid intake cycle. To reduce such error, a low-pressure gradient system can use a reduced maximum velocity. However, to operate at a reduced velocity and still achieve a desired flow rate (or other flow objective) during a given intake time requires an increase in acceleration. That is, if constrained to a given intake time, increasing acceleration serves to decrease the maximum velocity needed to accomplish a complete motor move (i.e., a full draw stroke of the motor's piston). The torque available at a given motor velocity, though, limits the extent to which the acceleration rate can increase. Generally, more torque is available at the low end of the range of motor velocities than at the high end of the range.

In accordance with the present invention, an intake velocity profile is developed to make optimal use of the motor's available torque over the range of motor velocities (i.e., zero to the desired terminal velocity). This optimized intake velocity profile represents the optimized acceleration curve along which the motor can operate in this range of motor velocities. A system controller uses the optimized intake velocity profile to determine when to issue pulses that tell the stepper motor when to step and at what rate to step. In general, the optimized intake velocity profile produces a higher acceleration (compared to constant acceleration intake velocity profiles) for most of the velocity range (particularly at the low end in the range of the velocities). As the velocity increases, the acceleration decreases, approximately following the optimized acceleration curve, which corresponds to the available motor torque along the range of velocities.

To minimize adjustments necessary to incorporate an optimized intake velocity profile in a system currently using a constant acceleration profile, the pump can use the constant acceleration intake profile for runs in which the desired terminal velocity is less than a defined threshold velocity. If the desired terminal velocity exceeds this threshold velocity, the system controller can then switch to the optimized intake velocity profile.

Figure 1:
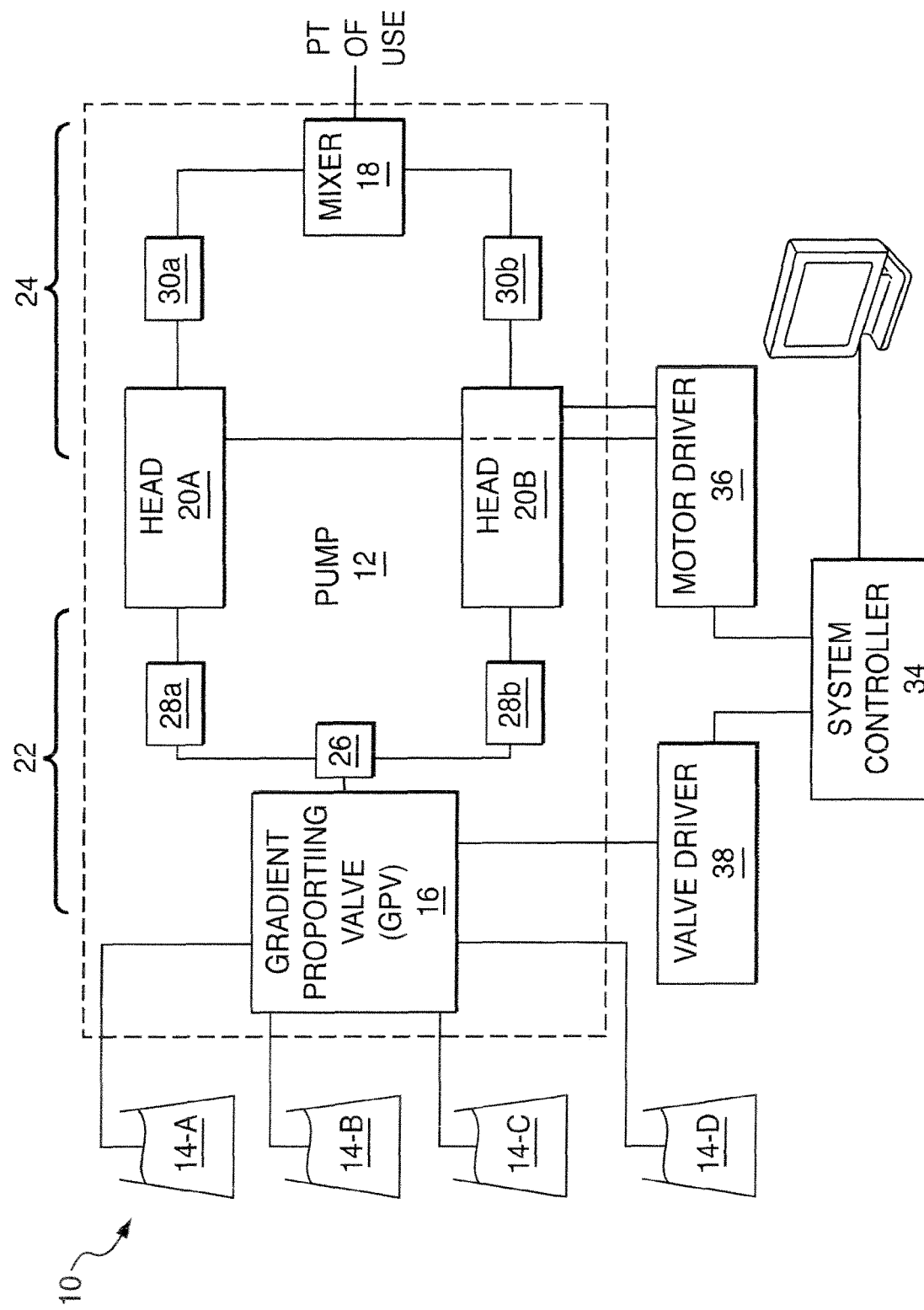
FIG. 1 is a block diagram of an embodiment of a system for metering liquids in controlled proportions, the system including a pump and a system controller for controlling the operation of the pump.

FIG. 1 shows an embodiment of a system 10 for metering liquids in controlled proportions and for delivering a resultant mixture to a point of use. The system 10 includes a low-pressure gradient pump 12 connected to a plurality of reservoirs 14-A, 14-B, 14-B, 14-D (generally, 14), each holding a fluid (typically a liquid solvent, or a gas). The pump 12 includes a gradient proportioning valve (GPV) 16, a mixer 18, and a pair of substantially identical pump heads 20a, 20b (generally, 20). In one embodiment, the pump is implemented using the 2545 Quaternary Gradient Module, manufactured by Waters Corp. of Milford, Mass. The pump 12 has an intake side 22 and a delivery side 24. On the intake side, each pump head 20a, 20bb is connected to the GPV 16 through an inlet manifold valve 26 and a first check valve 28a, 28b, respectively, and, on the delivery side 24, to the mixer 18 through a second check valve 30a, 30b, respectively.

In addition, the system 10 has a system controller 34 that is in communication with the GPV 16 through a valve driver 38 and with the pump heads 20 through a motor driver 36. A host computing system 40 is in communication with the system controller 34 by which a user can download parameters to memory (FIG. 3) of the system controller 34, including the intake velocity profiles described herein.

Figure 2:
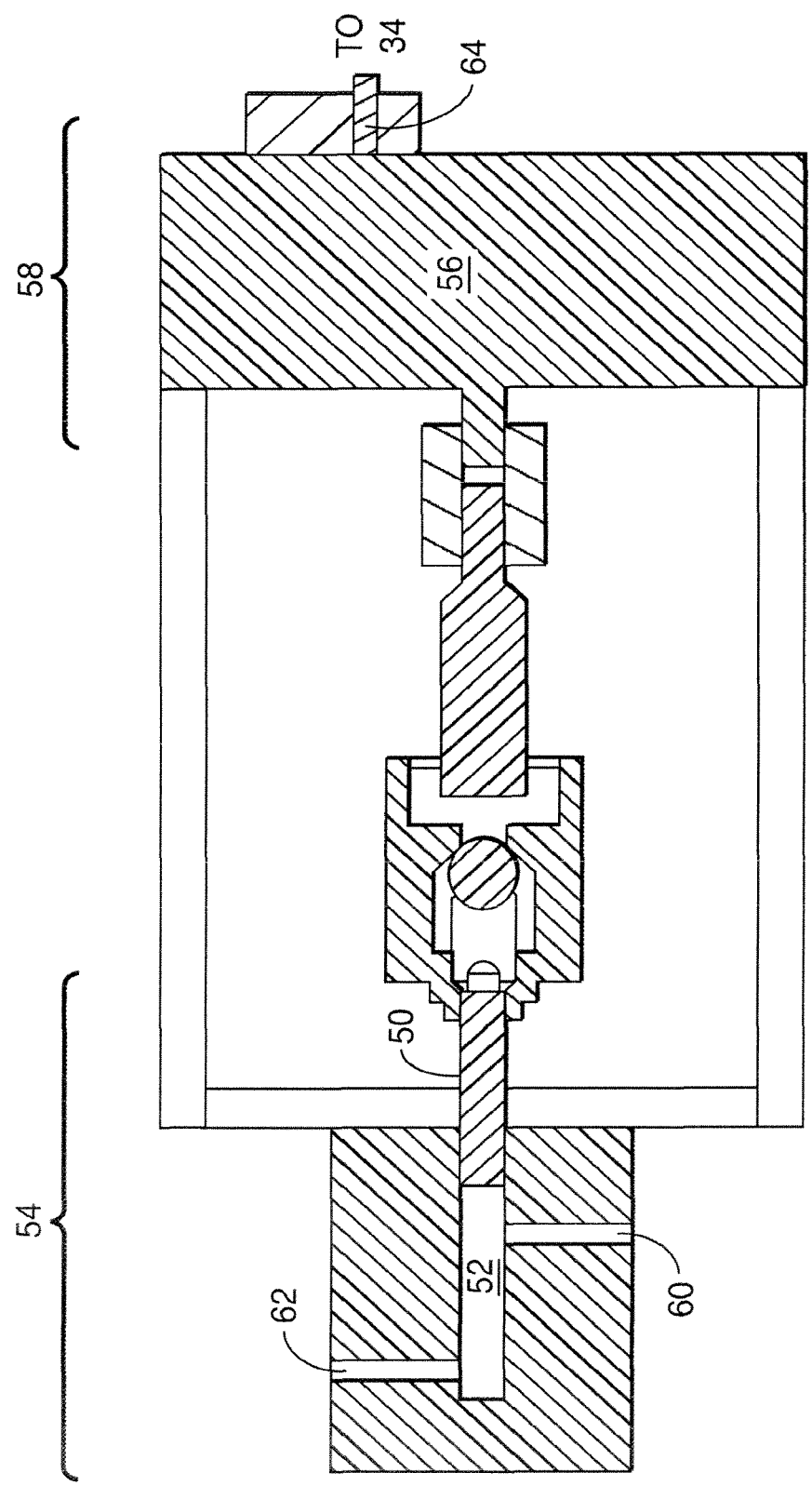
FIG. 2 is a diagram of an embodiment of a representative pump head in the pump of FIG. 1, the pump head including a stepper motor coupled to a plunger mechanism for reciprocal movement within a chamber that receives and delivers fluid.

The motor driver 36 is in communication with each pump head 20 to control a microstep-motor-driven piston or plunger (FIG. 2). Under the control of the system controller 34, the motor driver 36 sends pulses to the pump heads 20 that control stepwise behavior of the stepper motor in accordance with an intake velocity profile (e.g., an optimized intake velocity profile). In one embodiment, a pulse moves the motor 1 microstep (1/10th of a full step). The micro-stepping rate can be changed through firmware.

The GPV 16 accommodates the intake of fluid from the reservoirs 14 for mixing in desired proportions to form a liquid composition. The GPV 16 includes an inlet for each reservoir 14, an inlet valve (not shown) for controlling each flow of fluid being drawn into one of the inlets, and a common outlet through which fluid flows from the GPV 16 to the inlet valve manifold 26. At the inlet valve manifold, the sample is injected into the fluid composition provided by the GPV 16. A conduit for transporting fluid, for example, a tube, extends from each reservoir 14 to one of the inlets of the GPV 16 and from the outlet of the GPV 16 to the intake side of the inlet valve manifold 26. Conduits connect the inlet valve manifold 26 to the first check valves 28a, 28b. Under the control of the system controller 34, the valve driver 38 sends pulses to the GPV 16 to actuate the individual valves sequentially at the appropriate times (in synchronization with certain steps of the motor).

During operation of the system 10, the pump heads 20 cooperate to draw solvents from the reservoirs 14 through the GPV 16 in metered proportions and to deliver a continuous flow to the mixer 18. The reciprocating plungers of the pump heads 20 repeatedly execute a draw stroke during an intake cycle and a delivery stroke during a delivery cycle. In addition, the reciprocating plungers operate in complementary fashion (i.e., 180 degrees out-of-phase): when one reciprocating plunger executes a draw stroke in order to pull fluid from the GPV 16, the other is executing a delivery stroke in order to push fluid to the mixer 18. The mixer 18 delivers a continuous flow of mixed fluids to the point of use, for example, a chromatographic column.

FIG. 2 shows a simplified diagrammatic representation of an embodiment of a pump head 20 (representative of the pump heads 20a, 20b). The pump head 20 includes a reciprocating piston or plunger 50 within the chamber 52 at a head end 54. A stepper motor 56 at a motor end 58 of the pump head 20 moves the plunger 50 within the chamber 52.

Opening into the chamber 52 is an inlet passage 60 and an outlet passage 62. Fluid is pulled into the chamber 52 through the inlet passage 60 during a draw stroke of the plunger 50, and pushed out of the chamber 52 through the outlet passage 62 during a delivery stroke. In FIG. 2, the plunger 50 appears in a position corresponding to the completion of a draw stroke or, conversely, at the start of a delivery stroke. Pulses from the system controller 34, which control the frequency and stroke length of the plunger 50, arrive at the stepper motor 56 by way of a electrical signal conduit 64. In one embodiment, the length of a full stroke is 1.1 mils.

Figure 3:
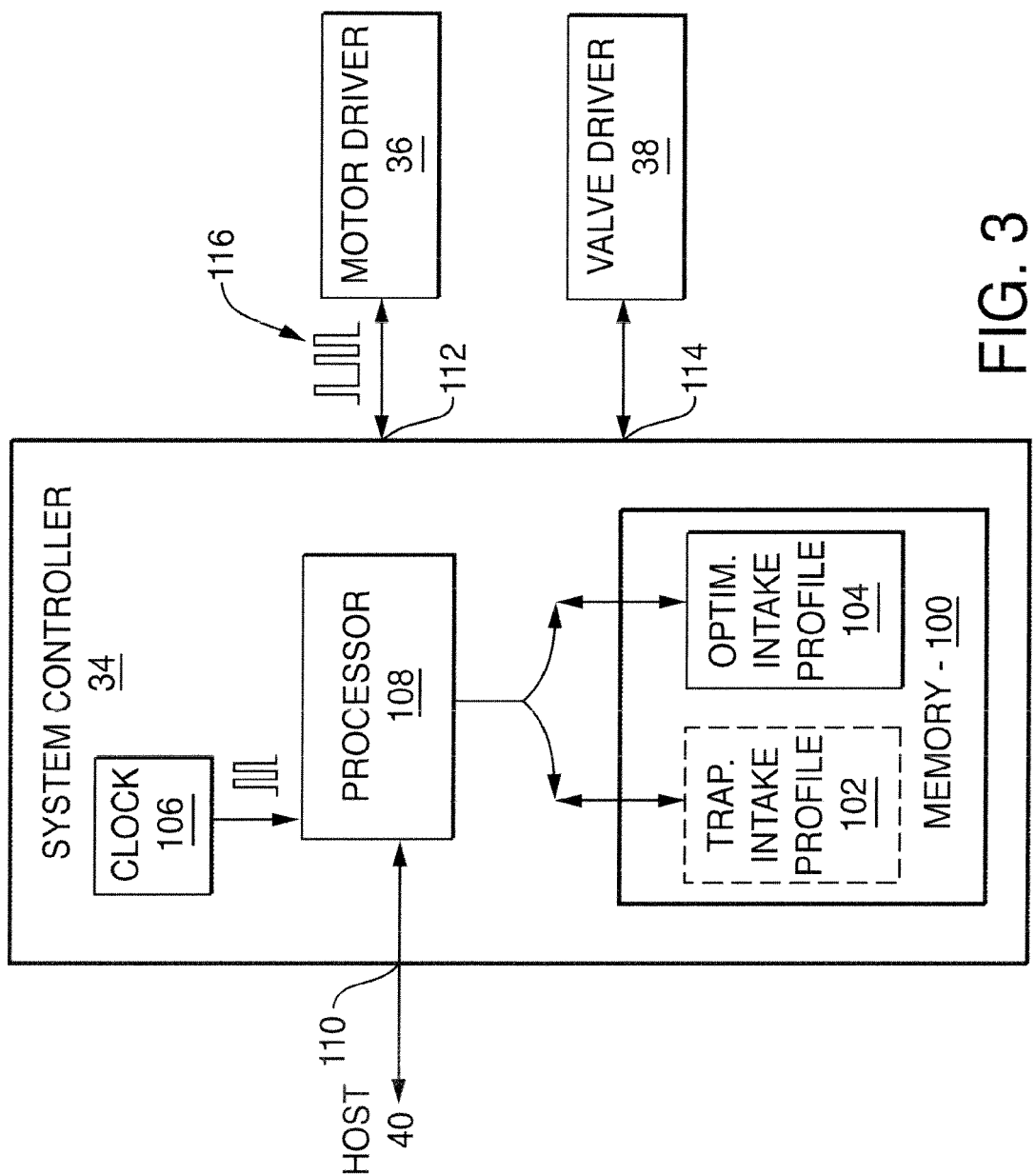
FIG. 3 is a block diagram of an embodiment of the system controller of FIG. 1.

FIG. 3 shows an embodiment of the system controller 34 of FIG. 1. The system controller 34 includes memory 100 storing a trapezoidal intake velocity profile 102 (described below) and an optimized intake velocity profile 104 of the present invention. Trapezoidal, as used herein to describe an intake velocity profile, is a metaphorical reference to the cyclical waveform shape for motor velocity during an intake cycle (FIG. 8B). The trapezoidal velocity waveform includes a linearly increasing velocity until the motor 56 attains a desired terminal velocity, followed by a constant velocity at the desired terminal velocity for a predetermined period, and then by a linearly decreasing velocity until the velocity reaches zero. The corresponding acceleration curve that produces this trapezoidal velocity waveform uses constant acceleration until the stepper motor reaches the desired velocity followed by constant deceleration after the stepper motor operates at the desired velocity for a given period (during which period the acceleration rate is equal to zero). Optimized, as used herein to identify an intake velocity profile, refers to the use of maximum acceleration based on available torque and a desired margin of operation over a range of motor velocities (i.e., zero to a predefined desired terminal velocity).

The intake velocity profiles 102, 104 are statically determined. A user of the host 40 downloads and stores the intake velocity profiles into the memory 100 of the system controller 34 before operating the pump 12. In general, the system controller 34 refers to an intake velocity profile to determine how to execute a motor move during an intake cycle (i.e., a draw stroke of the plunger 50 of a pump head 20). In one embodiment, the system controller 34 uses the trapezoidal intake velocity profile 102 to control the motor move when the desired terminal velocity is less than or equal to a threshold velocity and switches to the optimal intake velocity profile 104 when the desired velocity is greater than that threshold velocity. Although two intake velocity profiles are described, the system 10 can have multiple optimized intake velocity profiles to which the system controller 34 has access. In addition, the trapezoidal intake velocity profile 102 is optional; the system 10 does not require this profile 102 in order to practice the invention (accordingly, the trapezoidal intake velocity profile 102 is shown in phantom).

In addition, the system controller 34 includes a clock 106, a microprocessor 108, an input terminal 110 for receiving commands and information, for example, the intake velocity profiles, from the host computer 40 (FIG. 1), and output terminals 112, 114 for sending pulses to the motor driver 36 and, valve driver 38 respectively. The clock 106 provides the timing requisite for the microprocessor 108 to control properly the desired operation of the motor 56 (FIG. 2) in synchronized relationship with the actuating of the valves of GPV 16. The output produced by the system controller 34 includes a pulse train 116 representing the appropriate number and rate of motor steps for driving the stepper motor 56 at the desired velocity at a given point in time during an intake cycle in order to achieve the desired flow rate.

Figure 4:
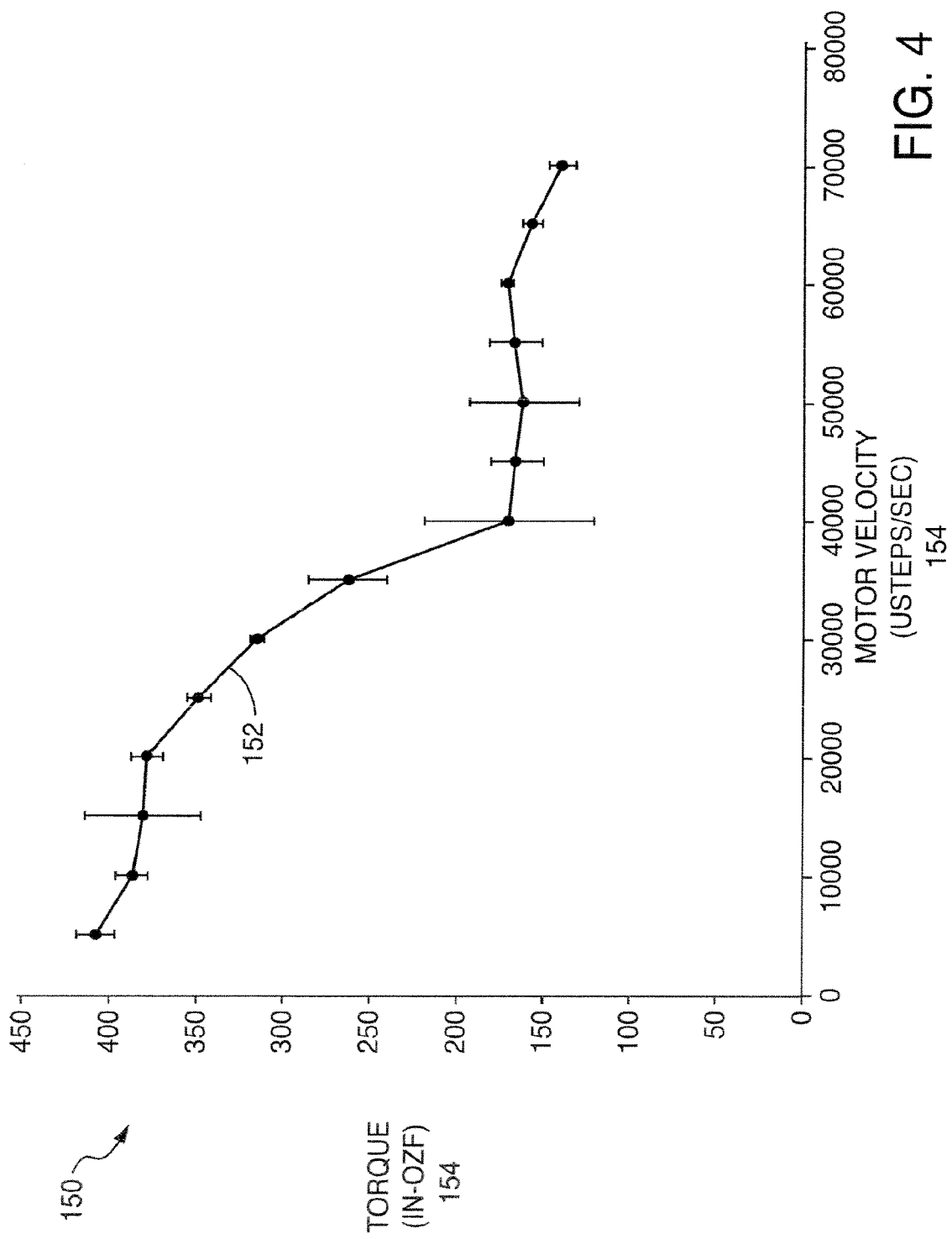
FIG. 4 is a graph of a torque-versus-speed curve for the stepper motor of FIG. 2.

The available torque of the stepper motor limits motor acceleration and varies according to the velocity at which the motor is currently operating. FIG. 4 shows a chart 150 illustrating an example of a torque-speed curve 152. It is to be understood that the illustrated torque-speed curve 152 is an example and that torque-speed curves are specific to the particular stepper motor being used. The particular illustrated torque-speed curve 152 corresponds to that of the stepper motor used in Waters Corp.'s 2545 Quaternary Gradient Module, which is the subject also of the other charts and plots described herein.

In the chart 150, torque is on the y-axis 154, expressed in torque units of in-ozf (inch-ounce force), and motor velocity is on the X-axis 156, expressed in units of microsteps (µsteps) per second. In general, the motor has greater torque at lower motor velocities, with the torque decreasing as the motor velocity increases (0-40000 µsteps/sec), and approximating a constant value (170 in-ozf) at higher motor velocities (40000-70000 µsteps/sec).

Figure 5:
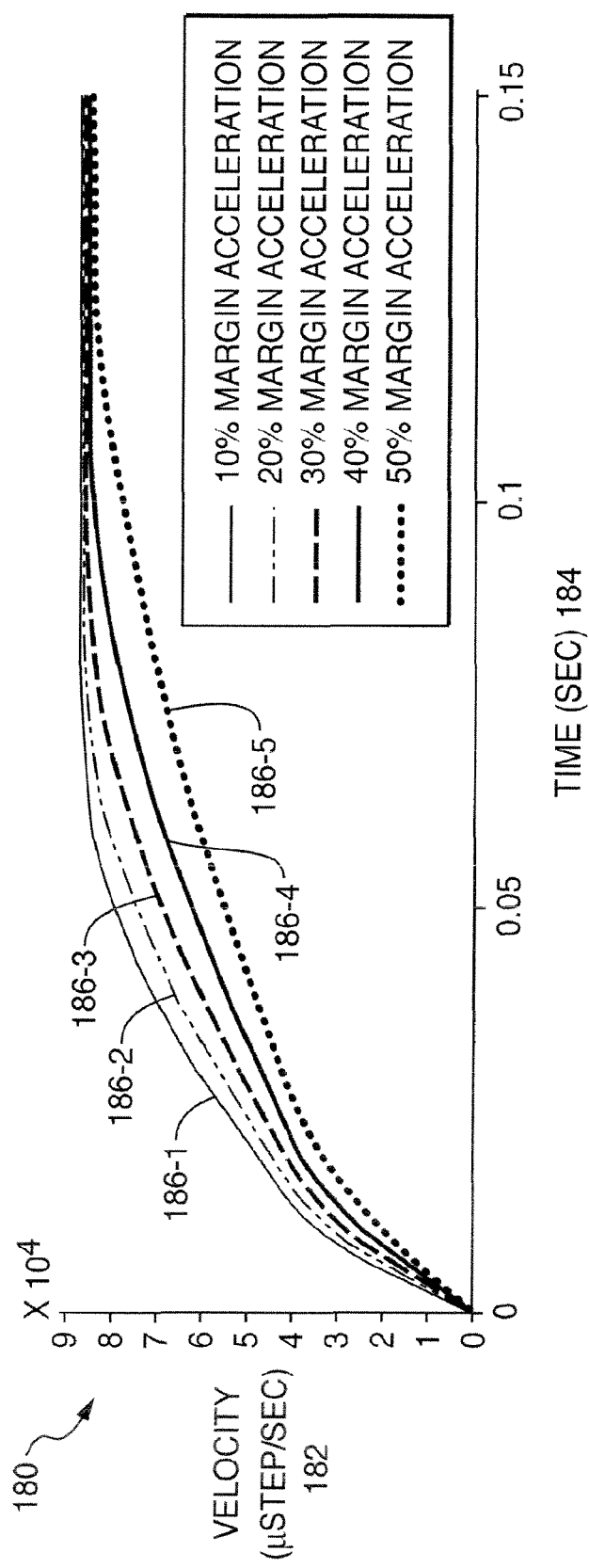
FIG. 5 is a chart that plots optimized velocity over time for different torque margins based on the torque-versus-speed curve of FIG. 3.

FIG. 5 shows a chart 180 that plots optimized maximum velocity over time based on the available torque of the motor. Motor velocity is on the y-axis, 182 and is expressed in µsteps per second. Time is on the x-axis 184, expressed in seconds. The chart 180 includes 5 different plots 186-1, 186-2, 186-3, 186-4, and 186-5 (generally, 186) representing different plots of motor velocity versus time, each plot corresponding to a different constant torque margin built into the maximum velocity of the stepper motor. The examples of torque margin shown are 10%, 20%, 30%, 40%, and 50%. The plots 186 illustrate a common pattern of operation across the various margins: the velocity rises substantially linearly to approximately 30000 usteps/sec (of the various plots, the plot 186-1 corresponding to the 10% margin rises most quickly, the one 186-5 with the 50% margin, least quickly) and then asymptotically approaches a maximum velocity of the motor (here, approximately 90000 usteps/sec). In general, the greater the torque margin, the lower the motor velocity at any given point in time.

Figure 6:
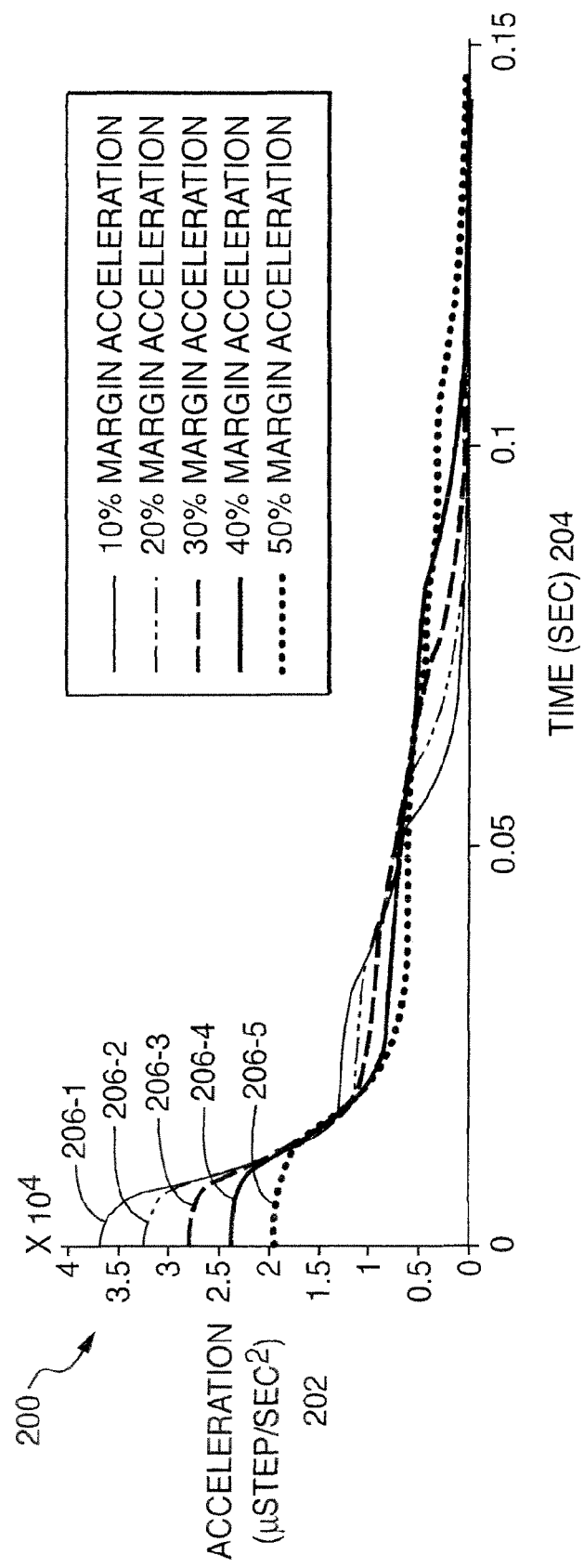
FIG. 6 is a chart that plots optimized acceleration over time for different torque margins based on the torque-versus-speed curve of FIG. 3.

FIG. 6 shows a chart 200 that plots optimized maximum acceleration over time based on the available torque of the motor. Acceleration is on the y-axis 202, expressed in µsteps per second squared. Time is on the x-axis 204, expressed in seconds. The chart 200 includes 5 different plots 206-1, 206-2, 206-3, 206-4 and 206-5 (generally, 206) representing different plots of acceleration versus time, each plot corresponding to a different constant torque margin built into the maximum acceleration of the stepper motor. The examples of torque margin shown are 10%, 20%, 30%, 40%, and 50%.

An example for an equation to determine the maximum available acceleration for the motor at a given velocity is as follows:

$$\alpha_{available} = [(100 - \text{margin})/100] * [T_{motor} - T_c - T_v(\omega)] / J_{sys}]$$

where $T_{motor}$ is the pullout torque of the motor, $T_c$ is torque associated with a constant load of the system, $T_v$ is torque associated with velocity, and $J_{sys}$ is the inertia of the system.

The plots 206 demonstrate a common pattern of operation across the various margins: initially the maximum possible acceleration (with a given margin) is approximately constant for a period, and then decreases non-linearly towards zero. Of the set of plots, the plot 206-1 corresponding to the 10% margin starts at the highest acceleration rate and decreases most quickly, and the plot 206-5 corresponding to the 50% margin starts with the lowest acceleration and decreases least quickly.

Figure 7:
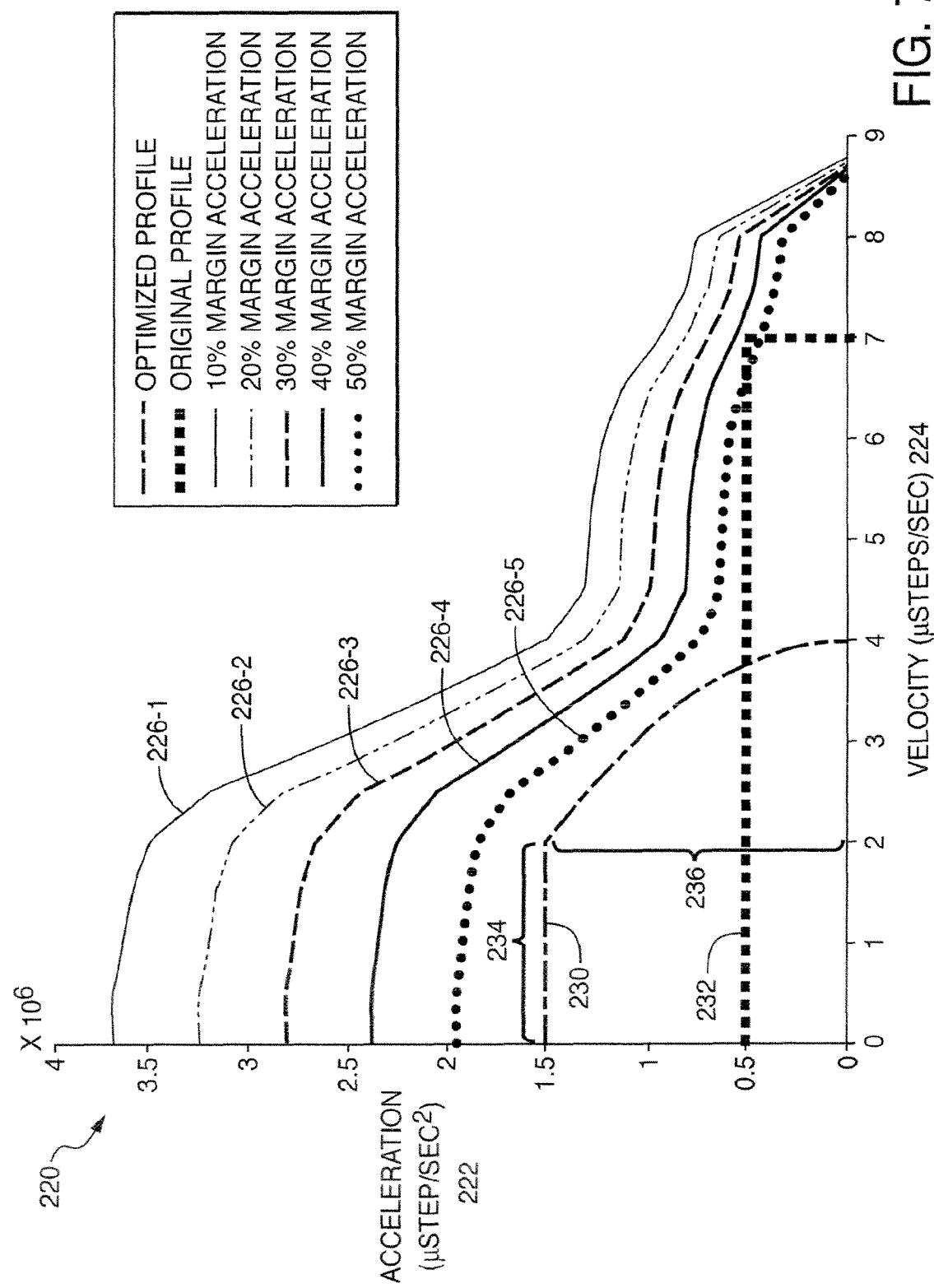
FIG. 7 is a chart that plots optimized acceleration versus velocity curves for different torque margins.

FIG. 7 shows a chart 220 that plots acceleration versus motor velocity based on the available torque of the stepper motor. The chart 200 presents the same data used to construct the charts shown in FIG. 5 and FIG. 6. Acceleration is on the y-axis 222, expressed in µsteps per second squared, and velocity is on the x-axis 224, expressed in µsteps per second. The chart 220 includes 5 different plots 226-1, 226-2, 226-3, 226-4, and 226-5 (generally, 226) representing different curves of maximum acceleration versus motor velocity. Each plot 226 corresponds to a different constant torque margin built into the acceleration of the stepper motor (10%, 20%, 30%, 40% and 50%). As shown, for each constant torque margin, the maximum acceleration rate at which the motor can be operated is greater at the low end of the range of motor velocities. In addition, for a given margin the maximum acceleration decreases as velocity increases, and for a given velocity, the maximum acceleration increases as the margin decreases. An optimized intake velocity profile can be generated from any one of the curves XX; each acceleration curve enables the stepper motor to be driven at a maximum acceleration over a range of velocities for a given constant torque margin. Other optimized intake curves can be produced (e.g., using different margins than those illustrated).

The chart 220 also illustrates a preferred optimized acceleration curve 230 and a constant acceleration curve 232. The preferred optimized acceleration curve 230 represents an optimized intake velocity profile for accelerating the motor to a desired terminal velocity of 40000 usteps per second. The acceleration curve 230 includes a linear portion 234 and an arcuate portion 236 designed to follow generally the shape of the other optimized curves 226. As implied by its position on the chart, operating the stepper motor in accordance with this preferred acceleration curve 230 ensures a margin of at least 50% throughout the intake cycle (the same profile used to accelerate the motor to the desired terminal velocity can be used to decelerate the motor to zero velocity). Deceleration can be faster than the acceleration because friction helps the motor slow down, thereby adding to the available torque.

The linear and arcuate portions 234, 236 of the preferred optimized acceleration curve 230 simplify the generation of table values for representing and storing the acceleration curve 230 in tabular form (as an optimized intake velocity profile stored in memory 100). Simple mathematical equations can represent each portion 234, 236 and be used to generate points along the preferred optimized acceleration curve 230. This process is less computationally intensive than extracting specific acceleration values from specific points on a less geometrically structured curve (such as the other curves 226), computing table values for each of these extracted values, and populating entries in a table with the computed values (e.g., using a text editor to populate the table directly or software for filling in the table with hard-coded values).

The constant acceleration curve 232 represents the stage of the trapezoidal intake velocity profile during which the velocity constantly increases towards the desired terminal velocity. The constant acceleration curve 232 crosses a range of velocities from 0 to 70000 usteps/sec². As is evident by the area 238 between the preferred optimized acceleration curve 230 and the constant acceleration curve 232, operating the stepper motor in accordance with the constant acceleration curve 232 does not utilize the motor at its fullest torque capabilities. For much of its velocity range, the constant acceleration curve provides more than a 50% margin until the curve approaches the high end of the range (approximately 70000 usteps per sec), at which point the constant acceleration curve 232 no longer maintains the 50% margin (i.e., where it crosses the optimized acceleration curve 226-5 based on the 50% margin and closely approaches the 40% margin acceleration curve 226-4).

Figure 8A:
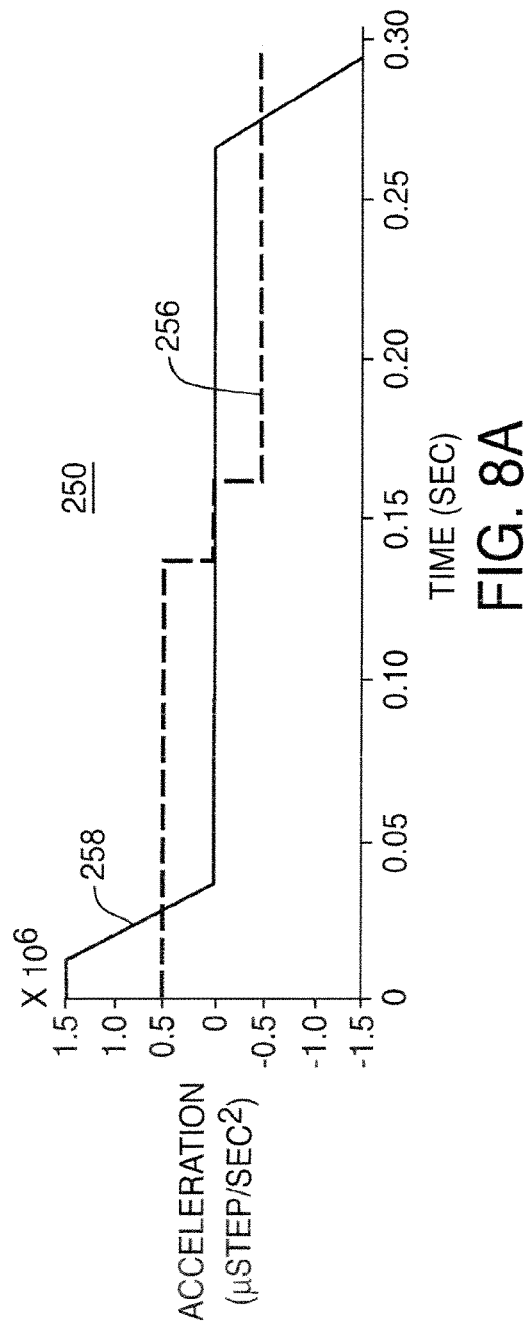
Figure 8B:
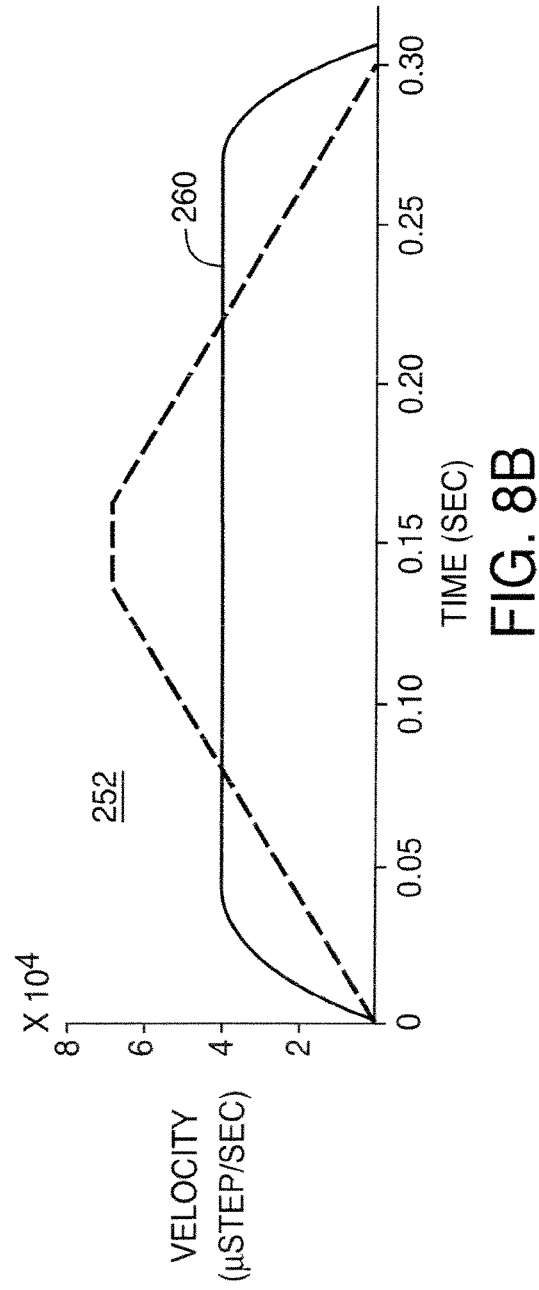

FIG. 8A, FIG. 8B, and FIG. 8C show three charts 250, 252, and 254, respectively. Chart 250 is of acceleration (x-axis) over time (x-axis); chart 252 is of velocity (y-axis) over time (x-axis); and chart 254 is of motor position in units of steps (y-axis) over time (x-axis). Each chart provides a comparison between motor operation in accordance with the trapezoidal intake velocity profile 104 representing the constant acceleration curve 232 (plots are in dashed lines) and the optimized intake velocity profile 230 representing the preferred optimized acceleration curve 232 (plots are in solid lines). The plots of the charts 250, 252, and 254 are aligned over time. Again, these plots are based on the stepper motor used in Waters Corp.'s 2545 Quaternary Gradient Module. The intake cycle takes approximately 0.30 seconds; the intake cycle is only 3% longer for the optimized intake velocity profile than for the trapezoidal intake velocity profile, despite the terminal velocity of the optimized intake velocity profile being 43% less than that of the trapezoidal intake velocity profile.

As shown in the acceleration chart 250, the stepper motor, when operating according to the trapezoidal intake velocity profile during an intake cycle, undergoes constant acceleration (approximately 40000 usteps per second squared) until the motor velocity (see chart 252) reaches a desired velocity (70000 usteps per second). When the motor is operating at the desired velocity, the system controller drops the acceleration immediately to zero, and maintains the acceleration at zero for a predetermined period. Then, the system controller decelerates the stepper motor at a constant rate until the motor velocity reaches zero.

The acceleration chart 250 also shows that when operating according to the preferred optimized intake velocity profile 104 during an intake cycle, the stepper motor initially operates at a constant acceleration for a defined period, and then linearly decreases over time until the motor reaches a desired motor velocity. The desired motor velocity is significantly lower (here, 40000 usteps/sec vs. 70000 usteps/sec) than the desired motor velocity produced by the trapezoidal intake velocity profile. Because error is proportional to velocity for low-pressure gradient systems, being able to operate at a low velocity (relative to 70000 usteps/sec) is particularly beneficial for reducing such error. The linear decrease in acceleration corresponds to the arcuate portion 234 of the acceleration curve shown in FIG. 7 and accurately approximates the 50% margin curve 226-5 of FIG. 7 with reasonable computational complexity. Other functions can be used to approximate the margin curve without departing from the principles of the invention.

The velocity graph 252 shows the trapezoidal velocity curve produced by the constant acceleration curve 256 described in the acceleration chart 250. Velocity increases linearly until the motor attains the desire terminal velocity, remains constant at the terminal velocity for a specific period, and then decreases linearly to zero. Because of the fixed duration of the intake cycle, the motor does not operate long at the terminal velocity before having to begin deceleration. Thus, for most of the intake cycle the motor is operating at a changing speed.

In addition, the velocity graph 252 shows the velocity curve 260 produced by following the optimized acceleration curve 258 described in the acceleration graph 250. Within 40 ms, the velocity increases to the desired terminal velocity. After remaining constant at that terminal velocity for a specified period, the motor decelerates to zero velocity. As is evident from the velocity graph, when operating according to the optimized intake velocity profile 104, the motor operates at the desired terminal velocity for a greater portion of the intake cycle than when operating according to the trapezoidal intake velocity profile. Accordingly, the motor takes more steps when operating at a constant velocity (zero acceleration) using the optimized intake velocity profile than when using the trapezoidal intake velocity profile. Advantageously, operating the system with less acceleration poses fewer problems associated with the proper metering of fluids at the GPV.

The position chart 254 shows two curves 264, 266 corresponding to the motor step position when operating according to the trapezoidal intake velocity profile 102 and when according to the optimized intake velocity profile 104, respectively. The motor has approximately 11 thousand steps. As shown, the curve 266 for the optimized intake velocity profile is more linear than the curve 264 for the trapezoidal intake velocity profile across these 11 thousand steps. Thus, the intervals for causing stepwise movement of the motor occur more regularly under the optimized intake velocity profile than for the trapezoidal intake velocity profile. Correspondingly, the opening and closing of valves in the GPV can be more consistently regulated to synchronize such events with the stepping of the motor.

As described above in connection with FIG. 2, the processor 108 of the system controller 34 accesses the memory 100 to acquire the optimized intake velocity profile representing the optimized acceleration curve and to issues pulses to the motor in accordance with that optimized intake velocity profile. Representing this optimized intake velocity profile in memory can be implemented in a variety of ways.

One embodiment uses an acceleration table to store non-dimensional data values that represent the optimized intake velocity profile (and, thus, the optimized acceleration curve to be followed by the motor). Each table entry corresponds to a step on the optimized acceleration curve. The first entry corresponds to the first step, the second entry corresponds to the second step, and so on. Each step in effect represents the elapsed time to the next motor pulse. The microprocessor 108 uses a pointer to maintain its current entry position in the table. After issuing a pulse based on the current table entry, the microprocessor 108 acquires the data value from the next entry and converts that value into the time (i.e., number of clock cycles) to delay issuing the next pulse.

Figure 9:
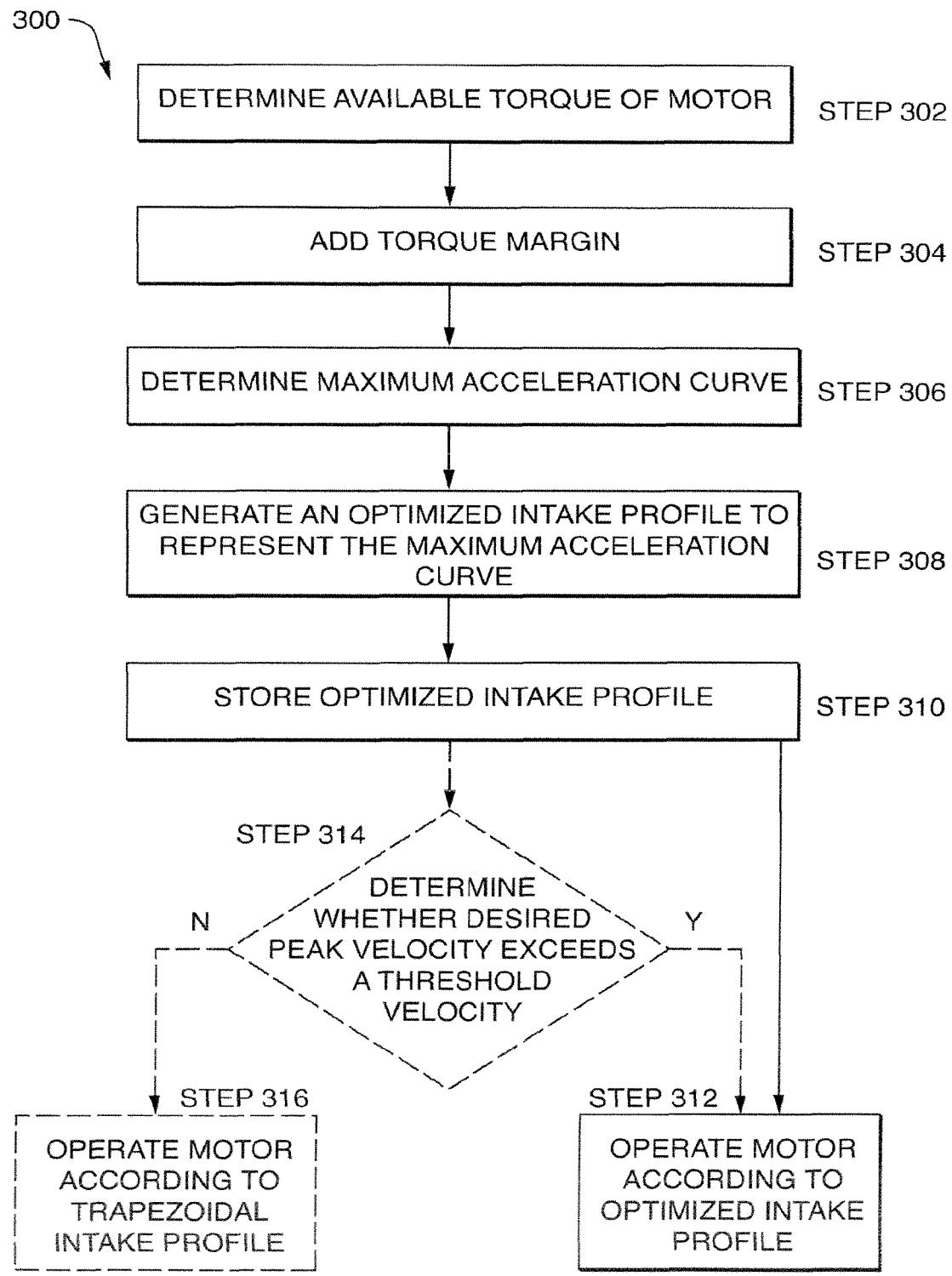
FIG. 9 is a flow chart of an embodiment of a process for operating a stepper motor in accordance with the invention.

FIG. 9 shows an embodiment of a process 300 for operating a stepper motor of a low-pressure gradient system. At step 302, the available torque of the stepper motor is calculated at a plurality of motor velocities at which the stepper motor can operate during an intake cycle. Margin is built into the calculation of available torque (step 304). A maximum acceleration rate is calculated (step 306) for each motor velocity of the plurality of motor velocities at which the stepper motor can operate during the intake cycle based on the available torque of the stepper motor at that motor velocity. An optimized intake velocity profile is generated (step 308) based on the calculated maximum acceleration rates. The optimized intake velocity profile is stored (step 310) in memory of the system controller, for example, in tabular format. The stepper motor is accelerated (step 312) during the intake cycle in accordance with the intake velocity profile.

In one embodiment, shown in phantom, the system controller determines (step 314) whether the desired terminal velocity exceeds a threshold velocity. If the desired terminal velocity is greater than the threshold, the system controller uses (step 312) the optimized intake velocity profile, otherwise the system controller uses (step 316) the trapezoidal intake velocity profile.

Program code (or software) of the present invention may be embodied as computer-executable instructions on or in one or more articles of manufacture, or in or on computer-readable medium. A computer, computing system, or computer system, as used herein, is any programmable machine or device that inputs instructions and data, processes, and outputs commands, or data. In general, any standard or proprietary, programming or interpretive language can be used to produce the computer-executable instructions. Examples of such languages include C, C++, Pascal, JAVA, BASIC, Visual Basic, and Visual C++.

Examples of articles of manufacture and computer-readable medium in which the computer-executable instructions may be embodied include, but are not limited to, a floppy disk, a hard-disk drive, a CD-ROM, a DVD-ROM, a flash memory card, a USB flash drive, an non-volatile RAM (NVRAM or NOVRAM), a FLASH PROM, an EEPROM, an EPROM, a PROM, a RAM, a ROM, a magnetic tape, or any combination thereof. The computer-executable instructions may be stored as, e.g., source code, object code, interpretive code, executable code, or combinations thereof. Further, although described predominantly as software, embodiments of the described invention may be implemented in hardware (digital or analog), software, or a combination thereof.

While the invention has been shown and described with reference to specific preferred embodiments, it should be understood by those skilled in the art that various changes in form and detail may be made therein without departing from the spirit and scope of the invention as defined by the following claims. For instance, although described herein with respect to low-pressure gradient pumps, the principles of the invention apply also to high-pressure mixing pumps (e.g., Waters Corp.'s 2525 AutoPurification pumps and Waters Corp.'s 2545 high-pressure mixing pumps).

What is claimed is:

1. A method for operating a stepper motor coupled to a reciprocating plunger mechanism of a fluidic pumping system during a fluid intake cycle to pump fluid into the pumping system, comprising:
    measuring available torque of the stepper motor across a range of motor velocities within which the stepper motor will operate during the fluid intake cycle;
    calculating a maximum acceleration rate for each of a plurality of motor velocities in the range of motor velocities based on the available torque of the stepper motor measured at that motor velocity;
    generating a fluid intake velocity profile based on the maximum acceleration rates calculated for the plurality of motor velocities; and
    accelerating the stepper motor during the fluid intake cycle in accordance with the generated fluid intake velocity profile to move the reciprocating plunger mechanism to pump fluid into the pumping system.

2. The method of claim 1, wherein the maximum acceleration rate determined for each motor velocity of the plurality of motor velocities includes an operating margin.

3. The method of claim 1, wherein the available torque of the stepper motor at each motor velocity of the plurality of motor velocities is a function of pullout torque of the stepper motor, load on the stepper motor, torque loss at that motor velocity, and motor inertia.

4. The method of claim 1, wherein accelerating the stepper motor during the fluid intake cycle in accordance with the generated fluid intake velocity profile includes:
initially accelerating the stepper motor at a constant acceleration rate until the stepper motor reaches a first motor velocity; and
after the stepper motor reaches the first motor velocity, accelerating the stepper motor at a decreasing acceleration rate to bring the stepper motor to a desired terminal velocity.

5. The method of claim 4, further comprising decelerating the stepper motor, after the stepper motor operates at the desired terminal velocity for a given duration, at an increasing deceleration rate until the motor velocity of the stepper motor reaches zero.

6. The method of claim 1, further comprising:
storing in memory a table of values representing the fluid intake velocity profile; and
translating the table of values into a series of pulses that controls the acceleration of the stepper motor over time in accordance with the fluid intake velocity profile.

7. The method of claim 1, wherein the fluid intake velocity profile is a first intake velocity profile and further comprising:
operating the stepper motor in accordance with a second intake velocity profile that causes the stepper motor to run at a constant acceleration rate until the stepper motor reaches a desired terminal velocity, followed by constant deceleration rate after the stepper motor operates at the desired terminal velocity for a given period;
determining whether the desired terminal velocity exceeds a threshold velocity; and
switching control of the stepper motor from the second intake velocity profile to the first intake velocity profile when the desired terminal velocity exceeds the threshold velocity.

8. A method for operating a pump in a pumping system, the pump having a stepper motor coupled to a reciprocating plunger mechanism, the stepper motor moving the plunger mechanism within a chamber into which fluid is drawn during a draw stroke of the plunger mechanism, the method comprising:
storing information, in memory, corresponding to a fluid intake velocity profile that represents an optimized acceleration curve based on available torque for operating the stepper motor over a range of motor velocities at which the stepper motor will operate during a fluid intake cycle;
dynamically accessing the memory during the fluid intake cycle to acquire the information that corresponds to the fluid intake velocity profile; and
issuing a series of pulses to the stepper motor based on the information accessed in the memory;
accelerating the stepper motor, in response to the series of pulses, such that the stepper motor accelerates during the fluid intake cycle in accordance with the optimized acceleration curve represented by the fluid intake velocity profile to move the reciprocating plunger mechanism to pump fluid.

9. The method of claim 8, wherein the optimized acceleration curve includes an operating margin.

10. The method of claim 8, wherein accelerating the stepper motor includes:
initially accelerating the stepper motor at a constant acceleration rate until the stepper motor reaches a first velocity; and
after the stepper motor reaches the first velocity, accelerating the stepper motor at a decreasing acceleration rate to bring the stepper motor to a desired terminal velocity.

11. The method of claim 10, further comprising decelerating the stepper motor after the stepper motor operates at the desired terminal velocity for a given period, wherein the decelerating occurs at an increasing deceleration rate until the velocity of the stepper motor reaches zero.

12. The method of claim 8, further comprising dynamically determining from the information that corresponds to the fluid intake velocity profile when to issue each pulse in the series of pulses.

13. The method of claim 8, wherein the fluid intake velocity profile is a first intake velocity profile and further comprising:
storing information corresponding to a second intake velocity profile that represents a constant acceleration curve in accordance with which, during a fluid intake cycle, the stepper motor undergoes constant acceleration until the stepper motor reaches a desired terminal velocity followed by constant deceleration after the stepper motor operates at the desired terminal velocity for a given period;
operating the stepper motor in accordance with the second intake velocity profile when the desired terminal velocity is less than a threshold velocity; and
switching to operating the stepper motor in accordance with the first intake velocity profile when the desired terminal velocity exceeds the threshold velocity.

14. A pumping system, comprising:
a pump having a stepper motor coupled to a reciprocating plunger mechanism, the stepper motor moving the plunger mechanism within a chamber into which fluid is drawn during a draw stroke of the plunger mechanism;
memory storing information corresponding to a fluid intake velocity profile, the fluid intake velocity profile representing an optimized acceleration curve based on available torque of the stepper motor across a range of motor velocities at which the stepper motor will operate during a fluid intake cycle;
a system controller having a processor that is in communication with the stepper motor to issue pulses thereto and with the memory to access dynamically during the fluid intake cycle the information representing the fluid intake velocity profile and to determine from the accessed information when to issue pulses to the stepper motor, the issued pulses causing the stepper motor to accelerate in accordance with the optimized acceleration curve represented by the fluid intake velocity profile and move the plunger mechanism to pump fluid.

15. The system of claim 14, wherein the optimized acceleration curve includes an operating margin.

16. The system of claim 15, wherein the available torque of the stepper motor is a function of pullout torque of the stepper motor, load on the stepper motor, torque loss, and motor inertia.

17. The system of claim 14, wherein during the fluid intake cycle the system controller initially accelerates the stepper motor at a constant acceleration rate until the stepper motor reaches a first velocity, and, after the stepper motor reaches the first velocity, accelerates the stepper motor at a decreasing acceleration rate to bring the stepper motor to a desired terminal velocity.

18. The system of claim 14, wherein during the fluid intake cycle the system controller decelerates the stepper motor, after the stepper motor operates at the desired terminal velocity for a given period, at an increasing deceleration rate until the motor velocity of the stepper motor reaches zero.

19. The system of claim 14, wherein the fluid intake velocity profile is a first intake velocity profile and the memory stores information corresponding to a second intake velocity profile, the second intake velocity profile representing an acceleration curve in accordance with, during an intake cycle, the stepper motor undergoes constant acceleration until the stepper motor reaches a desired terminal velocity followed by constant deceleration after the stepper motor operates at the desired terminal velocity for a given period; and wherein the system controller operates the stepper motor in accordance with the second intake velocity profile when the desired terminal velocity is less than a threshold velocity and switches to operating the stepper motor in accordance with the first intake velocity profile when the desired terminal velocity exceeds the threshold velocity.

* * * * *